(12) United States Patent
Grouchy et al.

(10) Patent No.: US 11,139,048 B2
(45) Date of Patent: Oct. 5, 2021

(54) DISCOVERING NOVEL FEATURES TO USE IN MACHINE LEARNING TECHNIQUES, SUCH AS MACHINE LEARNING TECHNIQUES FOR DIAGNOSING MEDICAL CONDITIONS

(71) Applicant: Analytics For Life Inc., Kingston (CA)

(72) Inventors: Paul Grouchy, Toronto (CA); Timothy Burton, Ottowa (CA); Ali Khosousi, Toronto (CA); Abhinav Doomra, North York (CA); Sunny Gupta, Toronto (CA)

(73) Assignee: Analytics For Life Inc., Toronto (CA)

( * ) Notice: Subject to any disclaimer, the term of this patent is extended or adjusted under 35 U.S.C. 154(b) by 1046 days.

(21) Appl. No.: 15/653,433

(22) Filed: Jul. 18, 2017

(65) Prior Publication Data

US 2019/0026430 A1 Jan. 24, 2019

(51) Int. Cl.

| | |
|---|---|
| *G06N 99/00* | (2019.01) |
| *G16H 50/20* | (2018.01) |
| *G06K 9/00* | (2006.01) |
| *G06F 16/56* | (2019.01) |
| *G16B 40/00* | (2019.01) |
| *G06N 3/04* | (2006.01) |

(Continued)

(52) U.S. Cl.
CPC ............ *G16B 40/00* (2019.02); *G06N 3/04* (2013.01); *G06N 3/086* (2013.01); *G06N 20/00* (2019.01); *G06F 17/00* (2013.01); *G06F 19/00* (2013.01)

(58) Field of Classification Search
CPC .......... G16B 40/00; G06N 20/00; G06N 3/04; G06N 3/086; G06F 17/00; G06F 19/00

USPC ...................................................... 706/1–62
See application file for complete search history.

(56) References Cited

U.S. PATENT DOCUMENTS

| | | |
|---|---|---|
| 6,513,025 B1 | 1/2003 | Rosen |
| 7,480,640 B1 | 1/2009 | Elad et al. |
| | (Continued) | |

FOREIGN PATENT DOCUMENTS

| | | |
|---|---|---|
| CN | 101785672 A | 7/2010 |
| CN | 103177114 A | 6/2013 |
| | (Continued) | |

OTHER PUBLICATIONS

International Search Report and Written Opinion received for related International Patent Application No. PCT/IB2018/000929, dated Jan. 7, 2019 (8 pages).

(Continued)

*Primary Examiner* — Brandon S Cole
(74) *Attorney, Agent, or Firm* — Perkins Coie LLP

(57) ABSTRACT

A facility providing systems and methods for discovering novel features to use in machine learning techniques. The facility receives, for a number of subjects, one or more sets of data representative of some output or condition of the subject over a period of time or capturing some physical aspect of the subject. The facility then extracts or computes values from the data and applies one or more feature generators to the extracted values. Based on the outputs of the feature generators, the facility identifies novel feature generators for use in at least one machine learning process and further mutates the novel feature generators, which can then be applied to the received data to identify additional novel feature generators.

16 Claims, 8 Drawing Sheets

$$F1_0 = A + C - D$$

$$F2_0 = \frac{A \cdot S(4) \cdot B}{D} + C + \sqrt{D}$$

(51) Int. Cl.
*G06N 3/08* (2006.01)
*G06N 20/00* (2019.01)
*G06F 17/00* (2019.01)
*G06F 19/00* (2018.01)

(56) References Cited

U.S. PATENT DOCUMENTS

| | | | |
|---|---|---|---|
| 7,792,770 | B1 | 9/2010 | Phoha et al. |
| 7,827,011 | B2 | 11/2010 | DeVaul et al. |
| 8,016,200 | B2 | 10/2011 | Kirby et al. |
| 8,041,651 | B2 | 10/2011 | Greer |
| 8,065,247 | B2 | 11/2011 | Schlottmann |
| 8,340,746 | B2 | 12/2012 | Syed et al. |
| 8,510,245 | B2 | 8/2013 | Stojadinovic et al. |
| 8,521,488 | B2 | 8/2013 | Kirby et al. |
| 8,688,603 | B1 | 4/2014 | Kurup et al. |
| 9,173,614 | B2 | 11/2015 | Sternickel et al. |
| 9,239,986 | B2 | 1/2016 | Lin et al. |
| 9,245,235 | B2 | 1/2016 | Chen et al. |
| 9,336,484 | B1 | 5/2016 | Iverson |
| 9,349,178 | B1 | 5/2016 | Itu et al. |
| 9,367,683 | B2 | 6/2016 | Kolacinski et al. |
| 9,576,262 | B2 | 2/2017 | Ganguly et al. |
| 9,582,781 | B1 | 2/2017 | Kearns et al. |
| 9,652,354 | B2 | 5/2017 | Filimonov et al. |
| 9,689,874 | B2 | 6/2017 | Blume et al. |
| 9,697,469 | B2 | 7/2017 | McMahon et al. |
| 9,811,795 | B1 | 11/2017 | Kearns et al. |
| 9,864,956 | B1* | 1/2018 | Sai ............... G06N 3/02 |
| 9,910,980 | B2 | 3/2018 | Kolacinski et al. |
| 10,127,214 | B2 | 11/2018 | Munro et al. |
| 10,366,346 | B2 | 7/2019 | Achin et al. |
| 10,405,219 | B2 | 9/2019 | Feldkamp |
| 10,417,523 | B2 | 9/2019 | Singh et al. |
| 2003/0018595 | A1 | 1/2003 | Chen et al. |
| 2003/0088565 | A1 | 5/2003 | Walter et al. |
| 2004/0204957 | A1 | 10/2004 | Afeyan et al. |
| 2005/0198182 | A1 | 9/2005 | Prakash et al. |
| 2006/0230006 | A1 | 10/2006 | Buscema |
| 2007/0047811 | A1* | 3/2007 | Itoh ............. G08B 13/19602 382/173 |
| 2010/0030780 | A1* | 2/2010 | Eshghi ............. G06F 16/56 707/758 |
| 2010/0063948 | A1 | 3/2010 | Virkar et al. |
| 2011/0119213 | A1 | 5/2011 | Elisseeff et al. |
| 2011/0172514 | A1* | 7/2011 | Lee ............. G06K 9/6262 600/408 |
| 2012/0029974 | A1 | 2/2012 | Councill et al. |
| 2012/0040861 | A1 | 2/2012 | Williams et al. |
| 2012/0078097 | A1 | 3/2012 | Wang et al. |
| 2013/0085773 | A1 | 4/2013 | Yao et al. |
| 2013/0103620 | A1 | 4/2013 | Yoon et al. |
| 2014/0143188 | A1 | 5/2014 | Mackey et al. |
| 2014/0344208 | A1 | 11/2014 | Ghasemzadeh et al. |
| 2014/0351183 | A1 | 11/2014 | Germain et al. |
| 2015/0003704 | A1* | 1/2015 | Nomura ............. G16H 30/20 382/128 |
| 2015/0127595 | A1 | 5/2015 | Hawkins, III et al. |
| 2015/0134315 | A1 | 5/2015 | Sarmiento et al. |
| 2016/0045120 | A1 | 2/2016 | Friedman et al. |
| 2016/0055426 | A1 | 2/2016 | Aminzadeh et al. |
| 2016/0180247 | A1* | 6/2016 | Li ............. G06Q 30/0277 706/12 |
| 2016/0300036 | A1 | 10/2016 | Ramazzotti et al. |
| 2016/0300156 | A1 | 10/2016 | Bowers et al. |
| 2016/0314580 | A1 | 10/2016 | Lloyd et al. |
| 2016/0350671 | A1 | 12/2016 | Morris, II et al. |
| 2017/0017900 | A1 | 1/2017 | Maor et al. |
| 2017/0169180 | A1 | 6/2017 | Hamann et al. |
| 2017/0249434 | A1 | 8/2017 | Brunner |
| 2018/0032678 | A1* | 2/2018 | Dandala ............. G06F 19/00 |
| 2018/0039731 | A1 | 2/2018 | Szeto |
| 2018/0060324 | A1 | 3/2018 | Clinton et al. |
| 2018/0137415 | A1 | 5/2018 | Steinberg et al. |
| 2018/0225391 | A1 | 8/2018 | Sali et al. |
| 2018/0293501 | A1 | 10/2018 | Ambati et al. |
| 2018/0349555 | A1* | 12/2018 | Devarakonda ......... G16H 10/60 |
| 2019/0080240 | A1 | 3/2019 | Andoni et al. |
| 2019/0087469 | A1 | 3/2019 | Zhang et al. |
| 2019/0130277 | A1 | 5/2019 | Andoni et al. |
| 2019/0138946 | A1 | 5/2019 | Asher et al. |
| 2019/0146759 | A1 | 5/2019 | Chiang et al. |
| 2019/0188536 | A1 | 6/2019 | Lei et al. |
| 2019/0200893 | A1 | 7/2019 | Grouchy et al. |
| 2019/0219994 | A1 | 7/2019 | Yan et al. |
| 2019/0295000 | A1 | 9/2019 | Candel et al. |

FOREIGN PATENT DOCUMENTS

| | | |
|---|---|---|
| CN | 105843896 A | 8/2016 |
| CN | 105912500 A | 8/2016 |
| CN | 106777891 A | 5/2017 |
| CN | 106777891 A1 | 5/2017 |
| CN | 107993723 A | 5/2018 |
| CN | 108090570 A | 5/2018 |
| CN | 108335756 A | 7/2018 |
| CN | 108875815 A | 11/2018 |
| CN | 108960269 A | 12/2018 |
| CN | 109117864 A | 1/2019 |
| CN | 109146076 A | 1/2019 |
| CN | 109217291 A | 1/2019 |
| CN | 109242021 A | 1/2019 |
| CN | 109273094 A | 1/2019 |
| CN | 109635955 A | 4/2019 |
| CN | 109711558 A | 5/2019 |
| CN | 109828836 A | 5/2019 |
| CN | 109948668 A | 6/2019 |
| CN | 110175644 A | 8/2019 |
| EP | 3048563 A | 7/2016 |
| JP | 2019079392 A | 5/2019 |
| KR | 20190078850 A | 7/2019 |
| WO | 2003040949 | 5/2003 |
| WO | 2005036180 | 4/2005 |
| WO | 2005048185 A1 | 5/2005 |
| WO | 2007044944 | 4/2007 |
| WO | 2009063463 | 5/2009 |
| WO | 2010044683 A1 | 4/2010 |
| WO | 2012103290 | 8/2012 |
| WO | 2012103290 A1 | 8/2012 |
| WO | 2016022438 A1 | 2/2016 |
| WO | 2016057001 A1 | 4/2016 |
| WO | 2016118513 A1 | 7/2016 |
| WO | 2016164680 A2 | 10/2016 |
| WO | 2016187711 A1 | 12/2016 |
| WO | 2017033164 | 3/2017 |
| WO | 2017053347 A1 | 3/2017 |
| WO | 2017059022 A1 | 4/2017 |
| WO | 2017120579 A1 | 7/2017 |
| WO | 2007147166 A2 | 12/2017 |
| WO | 2019129060 A1 | 7/2019 |
| WO | 2019179836 A1 | 9/2019 |

OTHER PUBLICATIONS

Bishop, Christopher M., "Pattern Recognition and Machine Learning." © 2006 Springer Science+Business Media, LLC. (758 pages).
Abdel-Aal R.E., "GMDH-based Feature Ranking and Selection for Improved Classification of Medical Data." Journal of Biomedical Informatics 38 (2005) 456-468. © 2005 Elsevier Inc. (13 pages).
Abdel-Aal R.E., "Improved Classification of Medical Data Using Abductive Network Committees Trained on Different Feature Subsets." Research Institute and the Department of Computer Engineering at King Fahd University of Petroleum and Minerals, Dhahran, Saudi Arabia. (33 pages).
Bach, Benjamin, et al., "Interactive Random Graph Generation with Evolutionary Algorithms." W. Didimo and M. Patrignani (Eds.): GD 2012, LNCS 7704, pp. 541-552, 2013. © Springer-Verlag Berlin Heidelberg 2013. (12 pages).
Abdel-Aal, R.E., "Improved Classification of Medical Data Using Abductive Network Committees Trained on Different Feature Subsets," Computer Methods and Programs in Biomedicine 80.2 (2005): 141-153, Elsevier.

(56) References Cited

OTHER PUBLICATIONS

Alhoniemi, E., et al., "Compact Modeling of Data Using Independent Variable Group Analysis," IEEE Trans. on Neural Networks 18.6 (2007):1762-1776.

Alonso et al., "Modelling Medical Time Series Using Grammar-Guided Genetic Programming," Industrial Conf. on Data Mining, Springer, 2008.

Araújo, "A New Evolutionary Morphological-Rank-Linear Approach for Time Series Prediction," IEEE Congress on Evolutionary Computation, CEC 2007, IEEE, 2007.

Arnaldo, I. et al., "Building Predictive Models via Feature Synthesis," GECCO '15, ACM, 2015, pp. 983-990.

Bishop, Christopher M., "Pattern Recognition and Machine Learning," Springer Science+Business Media, LLC, 2006, 758 pages.

Czajkowski et al., "An Evolutionary Algorithm for Global Induction of Regression Trees with Multivariate Linear Models," ISMIS 2011, LNAI 6804, pp. 230-239, 2011, Springer-Verlag.

Grosman et al., "Adaptive Genetic Programming for Steady-State Process Modeling," Computers & Chemical Engineering 28.12 (2004): 2779-2790, Elsevier.

Hadavandi et al., "Integration of Genetic Fuzzy Systems and Artificial Neural Networks for Stock Price Forecasting," Knowledge-Based Systems 23.8 (2010): 800-808, Elsevier.

Karabulut, E.M. and T. Ibrikci, "Analysis of Cardiotocogram Data for Fetal Distress Determination by Decision Tree Based Adaptive Boosting Approach," Journal of Computer and Communications, Scientific Research, published online Jul. 2014, pp. 32-37.

Spector, L. et al., "Evolution Evolves with Autoconstruction," ECADA 2016, ACM, 2016, pp. 1349-1356.

Tolstikhin et al., "AdaGAN: Boosting Generative Models," arXiv preprint, arxiv.org, arXiv:1701.02386 (2017), Jan. 9, 2017, https://arxiv.org/pdf/1701.02386.pdf.

Tuv, E. et al., "Feature Selection with Ensembles, Artificial Variables, and Redundancy Elimination," Journal of Machine Learning Research 10 (2009): 1341-1366.

Valdes, J., "Similarity-Based Neuro-Fuzzy Networks and Genetic Algorithms in Time Series Models Discovery," NRC/ERB-1093, NRC 44919, National Research Council of Canada, 2002.

Welling, M. et al., "Self Supervised Boosting," NIPS, 2002, pp. 665-672.

Wong et al., "Neural Networks and Genetic Algorithm for Economic Forecasting," Neuroprose—A Machine Readable Repository (1992).

International Search Report and Written Opinion received for counterpart International Patent Application No. PCT/IB2018/000902, dated Dec. 6, 2018, 17 pages.

Quade et al., "Prediction of Dynamical Systems by Symbolic Regression", Physical Review E 94(1), Jul. 2016 (16 pages).

Extended European Search Report received for counterpart European Patent Application No. 18835234.8, dated Mar. 22, 2021 (17 pages).

Szerlip, Paul A. et al., "Unsupervised Feature Learning through Divergent Discriminative Feature Accumulation" Proceedings of the Twenty-Ninth AAAI Conference on Artificial Intelligence (AAAI-2015), Jan. 30, 2015. pp. 2979-2985, XP055585712. Retrieved from the Internet: URL:https://eplex.cs.ucf.edu/papers/szerlip_aaai15.pdf (retrieved on May 6, 2019).

Asir D. et al., "Literature Review on Feature Selection Methods for High-Dimensional Data," International Journal of Computer Applications, [Online] vol. 136, No. 1, Feb. 17, 2016. pp. 9-17, XP055783802, DOI: 10.5120/jca2016908317. Retrieved from the Internet: URL:https://www.researchgate.net/profile/Asir-Antony-Danasingh/publication/295472880_Literature_Review_on_Feature_Selection_Methods_for_High-Dimensional_Data/links/57b697a108ae19a365fc59d0/Literature-Review-on-Feature-Selection-Methods-for-High-Dimensional-Data.pdf>.

Extended European Search Report received for related European Patent Application No. 18834730.6, dated Apr. 21, 2021 (13 pages).

Samanta B et al: "Artificial Neural Networks and Genetic Algorithm for Bearing Fault Detection," Soft Computing; A Fusion of Foundations, Methodologies and Applications. Springer, Berlin DE, vol. 10, No. 3, Feb. 1, 2006 (Feb. 1, 2006), pp. 264-271, XP019348667.

Sachnev Vasily et al: "Parkinson Disease Classification Based on Binary Coded Genetic Algorithm and Extreme Learning Machine," 2014 IEEE Ninth International Conference on Intelligent Sensors, Sensor Networks and Information Processing (ISSNIP). IEEE, Apr. 21, 2014 (Apr. 21, 2014), pp. 1-6, XP032604443.

Bhardwaj Arpit et al: "A Novel Genetic Programming Approach for Epileptic Seizure Detection," Computer Methods and Programs in Biomedicine, Elsevier, Amsterdam, NL, vol. 124, Nov. 2, 2015 (Nov. 2, 2015), pp. 2-18, XP029384416.

\* cited by examiner $$F2_0 = \frac{A \cdot S(4) \cdot B}{D} + C + \sqrt{D}$$

$$F1_0 = A + C - D$$

$$F1_1 = B \times (C + 7)$$

$$F1_1 = A \times (C - D)$$

| gen | $w_0$ | $w_1$ | $w_2$ | $w_3$ | $w_4$ | $w_5$ | $w_6$ | $w_7$ |
|---|---|---|---|---|---|---|---|---|
| 0 | 0.2 | 7 | 91 | 0.11 | 0.03 | 17 | 6 | 5 |
| 1 | 0.8 | 35 | 0.91 | 0.67 | 20 | 0.04 | 6 | 0.00 |
| 2 | 0.0 | 0.5 | 89 | 0.00 | 18 | 0.49 | 0.02 | 5 |
| ⋮ | ⋮ | ⋮ | ⋮ | ⋮ | ⋮ | ⋮ | ⋮ | ⋮ |
| $n$ | 72 | 0.07 | 7 | 0.27 | 1 | 0.55 | 95 | 0.06 |

DISCOVERING NOVEL FEATURES TO USE IN MACHINE LEARNING TECHNIQUES, SUCH AS MACHINE LEARNING TECHNIQUES FOR DIAGNOSING MEDICAL CONDITIONS

RELATED APPLICATIONS

This application is related to U.S. patent application Ser. No. 14/970,580, filed on Aug. 19, 2013, entitled "NON-INVASIVE METHOD AND SYSTEM FOR CHARACTERIZING CARDIOVASCULAR SYSTEMS," now U.S. Pat. No. 9,289,150; U.S. patent application Ser. No. 15/061,090, filed on Mar. 4, 2016, entitled "NON-INVASIVE METHOD AND SYSTEM FOR CHARACTERIZING CARDIOVASCULAR SYSTEMS;" U.S. patent application Ser. No. 15/588,148, filed on May 5, 2017, entitled "NON-INVASIVE METHOD AND SYSTEM FOR CHARACTERIZING CARDIOVASCULAR SYSTEMS;" U.S. patent application Ser. No. 13/605,364, filed on Sep. 6, 2012, entitled "SYSTEM AND METHOD FOR EVALUATING AN ELECTROPHYSIOLOGICAL SIGNAL," now U.S. Pat. No. 8,923,958; U.S. patent application Ser. No. 13/970,582, filed on Aug. 19, 2013, entitled "NON-INVASIVE METHOD AND SYSTEM FOR CHARACTERIZING CARDIOVASCULAR SYSTEMS FOR ALL-CAUSE MORTALITY AND SUDDEN CARDIAC DEATH RISK," now U.S. Pat. No. 9,408,543; U.S. patent application Ser. No. 15/207,214, filed on Jul. 11, 2016, entitled "NON-INVASIVE METHOD AND SYSTEM FOR CHARACTERIZING CARDIOVASCULAR SYSTEMS FOR ALL-CAUSE MORTALITY AND SUDDEN CARDIAC DEATH RISK;" U.S. patent application Ser. No. 14/295,615, filed on Jun. 4, 2014, entitled "NONINVASIVE ELECTROCARDIOGRAPHIC METHOD FOR ESTIMATING MAMMALIAN CARDIAC CHAMBER SIZE AND MECHANICAL FUNCTION;" U.S. patent application Ser. No. 14/077,993, filed on Nov. 12, 2013, entitled "NONINVASIVE ELECTROCARDIOGRAPHIC METHOD FOR ESTIMATING MAMMALIAN CARDIAC CHAMBER SIZE AND MECHANICAL FUNCTION;" U.S. patent application Ser. No. 14/596,541, filed on Jan. 14, 2015, entitled "NONINVASIVE METHOD FOR ESTIMATING GLUCOSE, GLYCOSYLATED HEMOGLOBIN AND OTHER BLOOD CONSTITUENTS," now U.S. Pat. No. 9,597,021; U.S. patent application Ser. No. 15/460,341, filed on Mar. 16, 2017, entitled "NONINVASIVE METHOD FOR ESTIMATING GLUCOSE, GLYCOSYLATED HEMOGLOBIN AND OTHER BLOOD CONSTITUENTS;" U.S. patent application Ser. No. 14/620,388, filed on Feb. 12, 2015, entitled "METHOD AND SYSTEM FOR CHARACTERIZING CARDIOVASCULAR SYSTEMS FROM SINGLE CHANNEL DATA;" U.S. patent application Ser. No. 15/192,639, filed on Jun. 24, 2016, entitled "METHODS AND SYSTEMS USING MATHEMATICAL ANALYSIS AND MACHINE LEARNING TO DIAGNOSE DISEASE;" U.S. patent application Ser. No. 15/248,838, filed on Aug. 26, 2016, entitled "BIOSIGNAL ACQUISITION DEVICE;" U.S. Provisional Patent Application No. 62/397,895, filed on Sep. 21, 2016, entitled "GRAPHICAL USER INTERFACE FOR CARDIAC PHASE-SPACE TOMOGRAPHY;" U.S. patent application Ser. No. 15/633,330, filed Jun. 26, 2017, entitled "NON-INVASIVE METHOD AND SYSTEM FOR MEASURING MYOCARDIAL ISCHEMIA, STENOSIS IDENTIFICATION, LOCALIZATION AND FRACTIONAL FLOW RESERVE ESTIMATION;" and U.S. patent application Ser. No. 15/653,441, filed concurrently herewith, entitled "DISCOVERING GENOMES TO USE IN MACHINE LEARNING TECHNIQUES." Each of the above-identified applications and issued patents is hereby incorporated by reference in its entirety.

BACKGROUND

Machine learning techniques predict outcomes based on sets of input data. For example, machine learning techniques are being used to predict weather patterns, geological activity, provide medical diagnoses, and so on. Machine learning techniques rely on a set of features generated using a training set of data (i.e., a data set of observations, in each of which an outcome to be predicted is known), each of which represents some measurable aspect of observed data, to generate and tune one or more predictive models. For example, observed signals (e.g., heartbeat signals from a number of subjects) may be analyzed to collect frequency, average values, and other statistical information about these signals. A machine learning technique may use these features to generate and tune a model that relates these features to one or more conditions, such as some form of cardiovascular disease (CVD), including coronary artery disease (CAD), and then apply that model to data sources with unknown outcomes, such as an undiagnosed patient or future weather patterns, and so on. Conventionally, these features are manually selected and combined by data scientists working with domain experts.

DETAILED DESCRIPTION

Figure 1B:
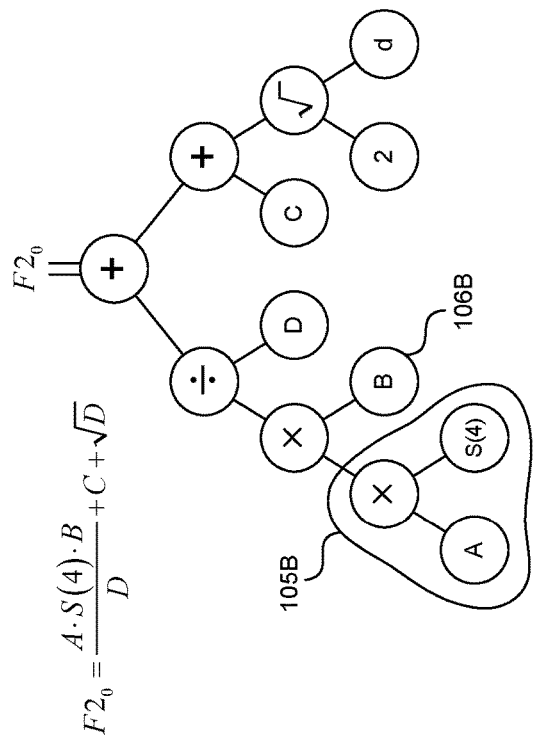
FIGS. 1A-1G are data structure diagrams that illustrate various types of mutations that can be applied to feature generators in accordance with some embodiments.

Because machine learning techniques rely on features to generate predictive models, the process of feature identification and generation typically is an important part of a machine learning process. The inventors have recognized that it can be expensive and time consuming manually to identify (and even more difficult to produce) features that provide a basis for generating more accurate models. Accordingly, the inventors have conceived and reduced to practice a facility that performs automatic feature discovery.

In some embodiments, the facility operates as part of a machine learning pipeline that constructs and evaluates predictive models, such as those for disease diagnosis, based on time-series and/or other signals, such as physiological signals. The machine learning process uses features to identify patterns within a training set of data and, based on these patterns, generates predictive models. These predictive models can be validated using validation data sets (i.e., data sets for which an outcome is known but that were not used to train the model) and applied to new input data in order to predict outcomes from the input data, such as providing a diagnosis for a medical condition, etc. As new data and new features are produced or acquired, the machine learning process improves upon the predictive capabilities of these models by incorporating new features and, in some cases, discarding others, such as those that are determined to be too similar to other features.

In some embodiments, the facility seeks to identify a set of feature generators that each extracts one or more values from each input data set and then combines and/or manipulates the extracted values. The facility evaluates feature generators by applying each of them to a set of training observations. For each feature generator, the set of values produced by performing the value extraction and combination/manipulation it specifies to each of the training observations is referred to as the feature generator's "feature vector." The facility compares these feature vectors against each other to assess their novelty (i.e., how different they are from other feature vectors). The feature generators that produced feature vectors identified as novel are added to the set of features available for use as inputs to models constructed and evaluated by the machine learning pipeline. Furthermore, each of the feature generators used to generate the feature vectors identified as novel are modified to produce a new generation of feature generators. The facility similarly evaluates the new generation of feature generators by assessing the novelty of the feature vectors they produce from training observations. The facility repeats this over the course of multiple generations to provide even more features for the machine learning process.

By way of example, the facility for discovering novel features to use in machine learning techniques can be used for a medical diagnosis predictive modeling task. In this example, the facility receives, for a number of patients or subjects, one or more sets of physiological data that relate to some type of physiological output or condition of the patient over a period of time (e.g., less than a second, on the order of a few seconds, about ten seconds, about 30 seconds and up to about five minutes, about an hour or more, etc.), such as electroencephalograms, and so on. These data may be received in real-time or near real-time concurrent or nearly concurrent with the operation of the facility, or they may be received at an earlier time. In some cases, the facility discards certain portions of the signal to ensure that the signals from each patient commence at a stable and consistent initial condition. Furthermore, the data may be normalized to remove potentially misleading information. For example, the facility can normalize the amplitude of signal data (e.g., transforming to a z-score), to account for variations in signal strength caused by sensor contact or other non-physiological data. As another example, in the case of a cardiac signal, the facility can perform peak search and discard any data before a first heartbeat identified in the signal and after a last heartbeat identified in the signal.

In some embodiments, the facility applies a set of feature generators to a set of signals to generate, for each combination of a signal and a feature generator, a feature value for the signal. Thus, each feature value is representative of some property of the underlying signal data. In one example, the facility receives patient data for each of 1000 patients and applies one or more feature generators to the data to generate, for each application of a feature generator to the data of a single patient, a feature value (or set of feature values). The facility collects the feature values generated by a single feature generator in a "feature vector," such that the feature vector stores one feature value per patient. Once the feature vectors are generated, they can be compared to determine how different each is relative to each of the other feature vectors. The facility computes a distance metric for each feature vector to assess the novelty of the corresponding feature generator. Based on the assessed novelty, the facility (1) provides the feature generators that produced the novel feature vectors to the machine learning process for the purpose of basing new predictive models on the provided feature generators and (2) modifies these feature generators to create a new generation of feature generators. The facility repeats this evolutionary process to identify even more novel features for use by the machine learning process.

In some embodiments, for each received set of data, the facility computes or identifies separate sets of one or more values from the data. For example, in the case of data generated as part of an electrocardiogram, the facility identifies global and local maxima and minima within the data, computes frequency/period information from the data, calculates average values of the data over certain period of time (e.g., the average duration and values generated during a QRS complex), and so on. In some cases, the facility transforms the received data and extracts sets of one or more values from the transformed data. The facility can transform received signal data in any number of ways, such as taking one or more derivatives of the data, taking one or more partial derivatives of the data, integrating the data, calculating the gradient of the data, applying a function to the data, applying a Fourier transform, applying linear or matrix transformations, generating topology metrics/features, generating computational geometry metrics/features, generating differential manifold metrics/features, and so on. In this manner, the facility generates multiple perspectives of the data in order to yield a diverse set of features. While these transformations are provided by way of example, one of ordinary skill will recognize that the data can be transformed in any number of ways.

In one example, the facility receives multiple input signals (e.g., input signals collected by different electrodes or leads connected to a patient, multimodal signals, such as signals from leads of wide-band biopotential measuring equipment and a channel of $S_pO_2$ (blood oxygen saturation), and so on) and/or transformed signals and extracts values from the signal data by computing, for each signal, an average value of the signal over the sampling period. In this example, four signals per patient are represented, although one of ordinary skill in the art will recognize that any number of signals may be monitored and/or received for processing and further analysis by the facility. Thus, in this example, the extracted data of each patient can be represented as a set of these average values over time, such as:

TABLE 1

| Patient | A | B | C | D |
|---------|------|-----|-----|-----|
| 1 | 0.24 | 0 | 0 | 30 |
| 2 | 0.2 | 0.6 | 4.2 | 5 |
| n | .32 | 2 | 4 | .02 |

Table 1 represents a set of average signal values (A, B, C, and D) for each of n patients. Although average values have been used here, one of ordinary skill in the art will recognize that any type of data can be extracted or computed from the underlying data signals, such as the amount of time that a signal exceeded a threshold value, the values for one signal while the value of another signal exceeded a threshold value, and so on.

In some embodiments, after data have been extracted from the received signal, the facility applies one or more feature generators to the received or generated data, such as the extracted data, the raw or preprocessed signal data, the transformed data, and so on. A feature generator receives as input at least a portion or representation of the signal data and produces a corresponding output value (or set of values) (i.e., a "feature"). One set of feature generators includes the following equations:

$$F1 = A + C - D, \quad (Eq\ 1)$$

$$F2 = \frac{A * S(4) * B}{D} + C + \sqrt{D}, \text{ and} \quad (Eq\ 2)$$

$$F3 = S(1) * D, \quad (Eq\ 3)$$

where each of A, B, C, and D represents a value extracted from a specific patient's data and S(t) represents, for each signal, the value of the signal at time t. In Eq 1, for example, F1 represents the name of the feature while the equation A+C−D represents the corresponding feature generator. In some cases, the facility employs composite feature generators in which one feature generator serves as an input to another feature generator, such as:

$$F4 = \frac{F1 * F2}{\sqrt[3]{F3}} + .057 \quad (Eq\ 4)$$

In this example, the facility applies feature generators to the extracted data of each patient represented in Table 1 to generate, for each feature generator, a feature vector of three values (one for each patient), such as those represented in Table 2 below:

TABLE 2

| Patient | F1 | F2 | F3 |
|---------|-------|--------|--------|
| 1 | −29.76 | 5.48 | 905.83 |
| 2 | −0.6 | 6.67 | 9.57 |
| ... | | | |
| n | 4.3 | 185.74 | 0.04 |

In this example, the facility has applied each feature generator F1, F2, and F3 to the extracted data shown in Table 1 to generate, for each feature generator, a corresponding feature vector that includes a value for each patient. For example, the feature vector generated by applying feature generator F1 to the extracted data includes a value of −29.76 for Patient 1, a value of −0.6 for patient 2, and so on. Thus, each feature vector represents, for a specific feature generator, a signature (not necessarily unique) for the corresponding feature generator based on at least a portion of each patient's physiological data (i.e., the patients represented in the physiological data to which the feature generators were applied). In some examples, feature generators are expressed using different structures or models, such as expression trees, neural networks, etc. One of ordinary skill in the art will recognize that the facility may employ any number of feature generators and any number of sets of physiological data (or portions thereof) in the generation of feature vectors. In some embodiments, the facility randomly selects a number of previously-generated feature generators for use in generating feature vectors rather than employing each and every available feature generator. In some embodiments, the facility creates and/or modifies feature generators by, for example, randomly generating expression trees, randomly assigning weights to connections within a neural network, and so on.

In some embodiments, after the facility generates a number of feature vectors, the facility employs some form of novelty search to identify the most "novel" feature vectors among the generated feature vectors. Novelty corresponds to how different a particular feature vector is from each of a comparison set of other feature vectors (made up of any feature vectors generated by the facility during a current iteration and feature vectors produced by feature generators selected in any earlier iteration); the greater the difference from the feature vectors of the comparison set, the greater the novelty. The facility uses a form of distance as a measure of novelty (i.e., how "far" each feature vector is from the other feature vectors). In this case, for each generated feature vector, the facility calculates the distance between that feature vector and each of the other generated feature vectors and performs an aggregation of the generated distance values, such as calculating an average or mean (e.g., arithmetic, geometric, harmonic, etc.) distance value for the feature vector, or a total (sum) distance between the feature vector and each of the other generated feature vectors, identifying a mode distance value, a median distance value, a maximum distance value for the feature vector, and so on. For example, using the feature vectors of Table 2 (for patients 1, 2, and n), the distances for each set of feature vectors could be calculated as such:

$$F1\text{-}F2 \text{ distance: } \sqrt{(-29.76 - 5.48)^2 + (-0.6 - 6.67)^2 + (4.3 - 185.74)^2} = 184.97,$$

$$F1\text{-}F3 \text{ distance: } \sqrt{(-29.76 - 905.83)^2 + (-0.6 - 9.57)^2 + (4.3 - 0.04)^2} = 936.23$$

$$F2\text{-}F3 \text{ distance: } \sqrt{(5.48 - 905.83)^2 + (6.67 - 9.57)^2 + (185.74 - 0.04)^2} = 919.70.$$

In this example, the total Euclidean distance between each of the feature vectors has been calculated as a means for calculating a difference between each of two vectors. In addition to the feature vectors generated by a current set (i.e., a current generation) of feature generators, the facility includes feature vectors produced by feature generators selected in an earlier generation. In some examples, the facility applies a weight, such as a randomly generated weight, to each of the feature vectors and/or normalizes each set of feature vectors prior to comparison. Thus, the distance measurements for each of the feature vectors in this example are as follows:

TABLE 3

| Feature Generator | Distance to F1 | Distance to F2 | Distance to F3 | Average Distance | MAX Distance |
|-----------|--------|--------|--------|--------|--------|
| F1 | — | 184.97 | 936.23 | 560.60 | 936.23 |
| F2 | 184.97 | — | 919.70 | 552.34 | 919.70 |
| F3 | 936.23 | 919.70 | — | 927.97 | 936.23 |

In this example, the facility identifies the most "novel" feature vectors based on the calculated distances, which act as a "novelty score" or "fitness score" for each of the feature vectors. The facility identifies the feature vectors with the greatest average distance to other vectors (e.g., the feature vector generated by F3), the feature vectors with the greatest MAX distance (e.g., the feature vectors generated by F1 and F3), and so on. In some examples, the number of novel feature vectors identified is fixed (or capped) at a predetermined number, such as five, ten, 100, 500, etc. In other examples, the number of novel feature vectors to be identified is determined dynamically, such as the top 10% of analyzed feature vectors based on novelty scores, any feature vectors having a novelty scores that is more than a predetermined number of standard deviations beyond a mean novelty score for the analyzed feature vectors, and so on. The feature generators that produced each of these identified novel feature vectors can then be added to the set of features available for use as inputs to models constructed and evaluated by the machine learning pipeline. Those models can be applied to patient data for, e.g., diagnostic, predictive, therapeutic, or other analytic, scientific, health-related or other purposes.

In some embodiments, in addition to providing the feature generators used to generate the identified novel feature vectors for use by the machine learning process, the facility randomly mutates or modifies the feature generators used to generate the identified novel feature vectors. Each mutation effects some change in the corresponding feature generator and creates a new version of the feature generator that can be used to contribute to a new generation of feature generators. The facility uses this new feature generator to generate new feature vectors, and then assesses the novelty of the new feature vectors. Moreover, the corresponding feature generator can be further mutated to continue this process of feature vector and feature generation creation. For example, a feature generator expressed in the form of an equation, such as $F1_0=A+C-D$, can be mutated by randomly selecting one or more element(s) of the equation and replacing the selected element(s) with other elements (e.g., randomly selected elements). In this example, the equation can be changed by replacing A with B to create $F1_1=B+C-D$ or replacing C-D with $\sqrt[3]{C-B^2}$ to create $F1_1=B+\sqrt[3]{C-B^2}$. In this case, the subscripted 0 and 1 have been included to represent a generational marker or count for each of the feature generators. In other words, $F1_0$ represents F1 above (Eq 1) at generation 0 (i.e., the first generation), $F1_1$ represents a mutated version of F1 at generation 1 (i.e., the second generation), and so on. In some cases, an earlier generation (or a transformation thereof) is included as an element in subsequent generations, such as $F2_1=\sqrt{F2_0}+C^2$ or $F2_n=\sqrt{F2_{n-1}}+C^2$ ($n\neq 0$).

Figure 1A:
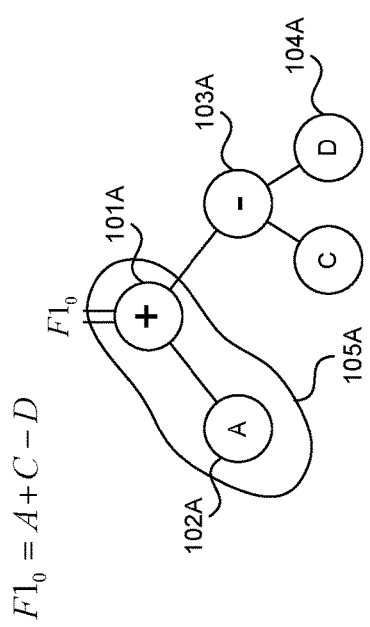
Figure 1D:
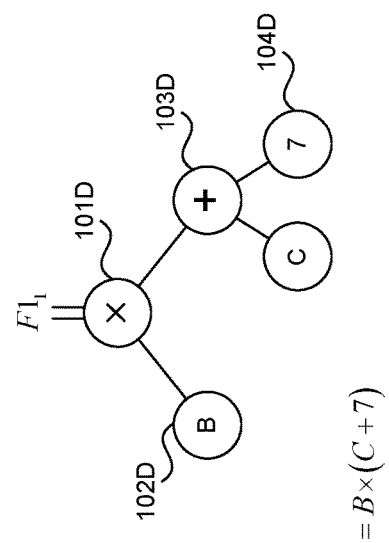
Figure 1C:
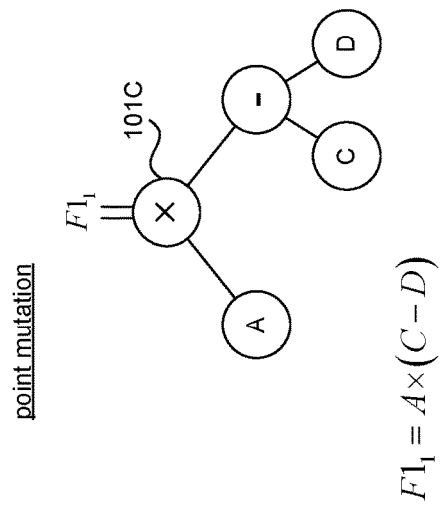

FIGS. 1A-1G include data structure diagrams that illustrate various types of mutations that can be applied to feature generators in accordance with some embodiments of the disclosed techniques. FIG. 1A represents an expression tree consistent with $F1_0$ while FIG. 1B represents an expression tree consistent with $F2_0$. In this example, each equation is expressed in the form of an expression tree. FIGS. 1C and 1D represent point mutations of $F1_0$. A point mutation to an expression tree causes a modification to one or more nodes in the expression tree, such as replacing one value with another value, transforming a value, replacing one operator with another operator, and so on. In FIG. 1C, the facility has replaced the addition operator 101A in FIG. 1A with node 101C, which represents the multiply operator; thus in this example $F1_1=A\times(C-D)$. In FIG. 1D, the facility has mutated each of nodes 101D, 102D, 103D, and 104D: node 101D has replaced addition operator node 101A with a multiplication operator, node 102D has replaced A of node 102A with B, node 103D has replaced subtraction operator node 103A with an addition operator, and node 104D has replaced D of node 104D with a value of 7; thus, in this example $F1_1=B\times(C+7)$.

Figure 1F:
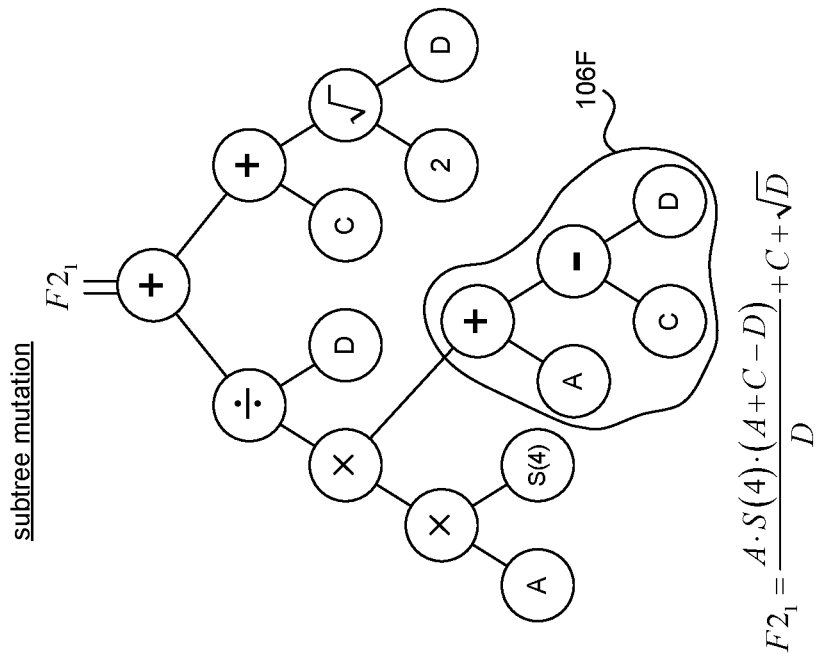
Figure 1E:
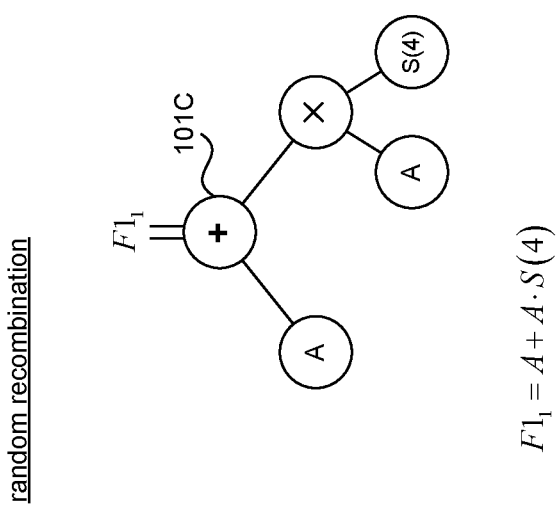

In some cases, the facility mutates a feature generator using one or more sexual reproduction techniques that allow for the combination of at least a portion of two different feature generators, such as a random recombination. FIG. 1E represents a "random recombination" mutation of $F1_0$. In a random recombination, subtrees from one or more expression trees are spliced together. In this example, subtree 105A is spliced together with subtree 105B, resulting in $F1_1=A+A*S(4)$ in this example. FIG. 1F represents a sub-tree mutation of $F2_0$. In a sub-tree mutation, a subtree of an expression tree is replaced with another subtree, such as a randomly-generated subtree, or a sub-tree selected (e.g., randomly) from another expression tree, and so on. In this example, subtree 106B (a single node) is replaced by the entire expression tree of FIG. 1A, resulting in $$F2_1 = \frac{A*S(4)*(A+C-D)}{D} + C + \sqrt{D}$$

in this example. One of ordinary skill in the art will recognize that the facility may apply other mutations to a feature generator and that any number of mutations can be applied to one or more elements of a feature generator simultaneously. For example, the facility can perform a subtree mutation to one element of an expression tree while also performing a point mutation to one or more nodes of the expression tree.

Figure 1G:
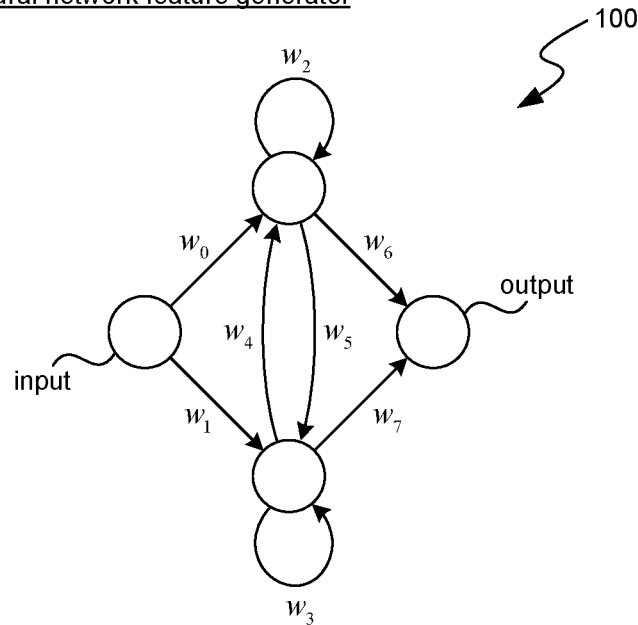

FIG. 1G represents a neural network 100 and plurality of sets 120 of corresponding connection weights ($w_0$-$w_7$), each set of connection weights corresponding to a different generation of the neural network. In some examples, an initial set of weights for the neural network is generated by, for each weight, invoking a random number generator to produce a value for the weight. Similarly, subsequent generations can be generated by again invoking the random number generator to produce a new value for the weight. In some embodiments, rather than simply invoking the random number generator to produce a new weight, the facility mutates each weight by applying some transformation to a previously-generated weight, such as w0(next)= w0(previous)*rand(MAX), where w0(next) represents the value of connection weight w0 in the generation being generated, w0(previous) represents the value of connection weight w0 in the most recent previous generation of connection weights, rand( ) represents a value produced by a random number generator, and MAX represents a maximum value constraint on the random number generator, which can provided by a user or generated automatically by the facility. One of ordinary skill in the art will recognize that each weight may be randomly generated and/or transformed in any number of ways.

In some embodiments, after mutating feature generators, the facility continues the novel feature discovery process by applying this next generation of feature generators to patient data, identifying novel feature vectors generated by feature generators of the new generation of feature generators, and providing the identified novel feature vectors for use in training and testing diagnostic models by a machine learning process. Furthermore, the facility further mutates the feature generators that produced novel features. The facility performs this process until a termination point is reached, such as when a generation of feature generators produces less than a threshold number of novel feature vectors (e.g., about five, ten, 100, etc.), a predetermined number of generations has been produced (e.g., about three, 15, 50, 1000, etc.), and so on.

In this manner, the facility provides new techniques for generating and identifying novel feature sets that can be used as part of a machine learning process to train diagnostic or predictive models. Accordingly, the disclosed techniques greatly improve the diagnostic ability and value of both 1) the predictive models generated via the machine learning processes and 2) the measurement devices and systems use to collect the underlying data, such as wide-band biopotential measuring equipment, by enhancing the value of the data produced by those devices and their ability to quickly and less invasively diagnose a condition (such as, e.g., CVD) or predict a future outcome, such as a likelihood of suffering a myocardial infarction. Thus, the disclosed techniques solve problems related to diagnosing or predicting outcomes based on analyzed data. For example, in the medical field these techniques can be used to obtain earlier and more accurate diagnoses, thereby reducing the overall number of tests required to verify the existence, or lack thereof, of a condition within a patient, the costs associated with additional tests required to make an initial diagnosis, and so on. Moreover, the disclosed techniques improve the effectiveness of diagnostic machine learning techniques by providing new ways to identify and produce novel features and, therefore, novel feature sets or vectors for training diagnostic and predictive models.

Figure 2:
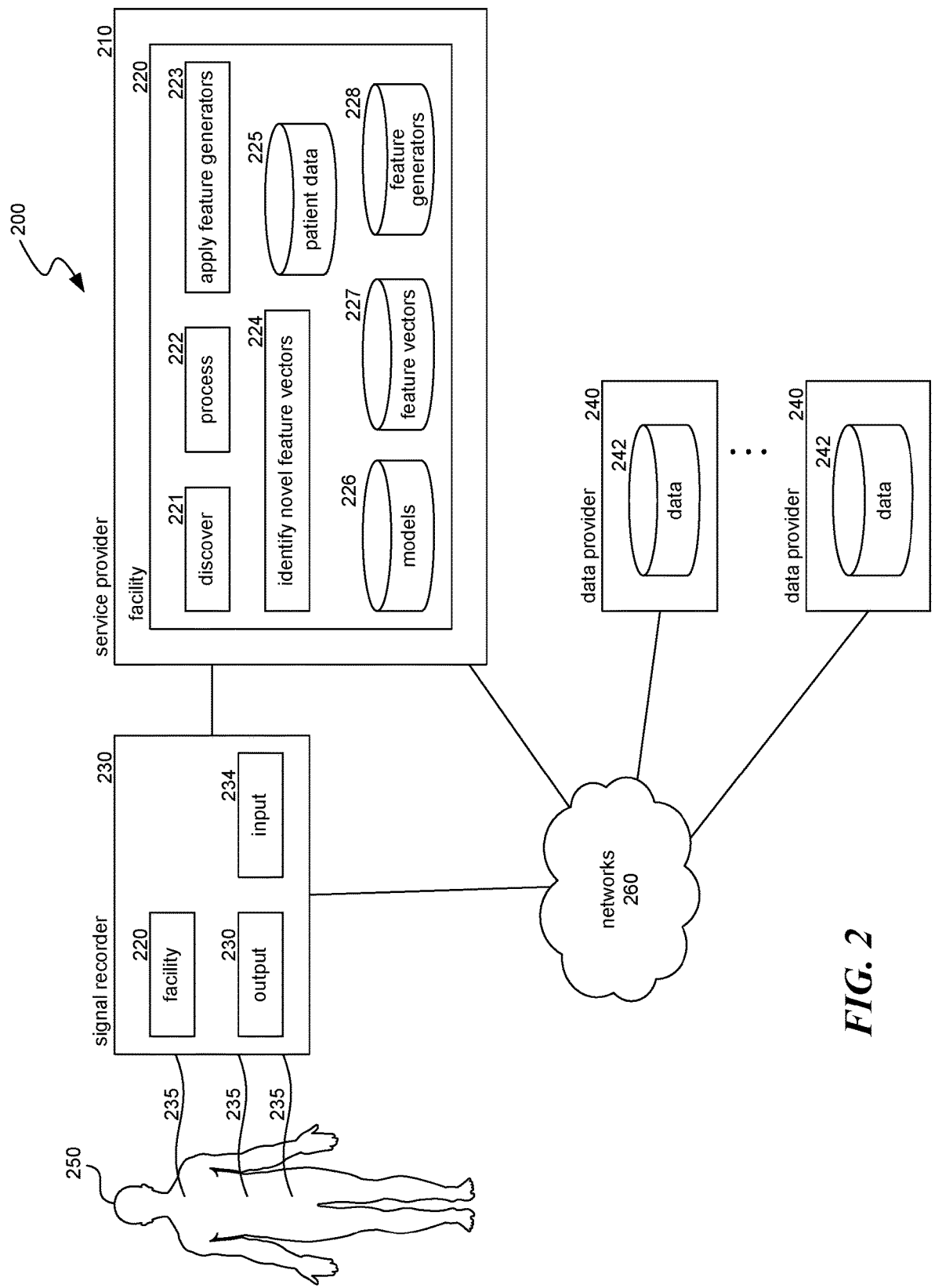
FIG. 2 is a block diagram illustrating an environment in which the facility operates in some embodiments.

FIG. 2 is a block diagram illustrating an environment 200 in which the facility operates in accordance with some embodiments of the disclosed technology. In this example, environment 200 includes service provider 210, signal recorder 230, data providers 240, patient 250, and network(s) 260. In this example, service provider includes facility 220, which includes discover component 221, process component 222, apply feature generators component 223, identify novel feature vectors component 224, patient data store 225, model store 226, feature vector store 227, and feature generator store 228. Discover component 221 is invoked by the facility to identify and mutate feature generators based on received data. Process component 222 is invoked by the discover component to process and transform patient signal data, such as raw signal data from a diagnostics machine (e.g., wide-band biopotential measuring equipment), 3-D image data, etc. Apply feature generators component 223 is invoked by the discover component to apply a set of one or more feature generators to the processed and transformed patient signal data. Identify novel feature vectors component 224 is invoked by the discover component to identify the most novel feature vectors from among a group of feature vectors generated by, for example, one or more feature generators. Patient data store 225 includes physiological patient data, such as raw physiological data, transformed physiological data, biographical information, demographic information, etc. These data may be stored anonymously to protect the privacy of each of the corresponding patients and may be processed and encrypted to ensure that its transmission and storage complies with any governing laws and their implementing regulations, such as the U.S. Health Insurance Portability and Accountability Act of 1996 (as amended), the European Data Protection Directive, the Canadian Personal Information Protection and Electronics Documents Act, the Australian Privacy Act of 1988, Japan's Personal Information Protection Act of 2015 (as amended), state and provincial laws and regulations, and so on. Model store 226 stores information about models generated by applying machine learning techniques to training data, such as the machine learning techniques described in Christopher M. Bishop, *Pattern Recognition and Machine Learning* (2006) (Library of Congress Control Number: 2006922522; ISBN-10: 0-387-31073-8), which is herein incorporated by reference in its entirety. Feature vector store 227 stores sets of feature vectors generated by applying one or more feature generators to a set of physiological data. Feature generator store 228 stores sets of feature generators that can be applied to patient physiological data and can include multiple generations of feature generators. In this example, a signal recorder 230 is connected to patient 250 via electrodes 235 and includes facility 220, one or more output devices 232, such as a monitor, printer, speaker, etc., and one or more input devices 234, such as settings controls, keyboard, biometric data reader, etc. Thus, as in this example, the facility can be configured to operate remotely from a patient and other diagnostics equipment and/or in conjunction with or part of the diagnostics equipment such as a wide-band biopotential measuring equipment (i.e., any device configured to capture unfiltered electrophysiological signals, including those with spectral components that are not altered). Accordingly, the facility can be configured to operate in real-time with the reading of physiological data and/or can be applied to previously recorded physiological data. Data providers 240, each of which includes a data store 242, can provide information for analysis or use by the facility such as, physiological patient data recorded off-site (e.g., at a hospital or clinic without access to a facility on premises, third-party data providers, etc.), feature vectors and/or feature generators produced or generated elsewhere, and so on. Network 260 represents communications links over which the various elements of environment 200 may communicate, such as the internet, a local area network, and so on.

In various examples, these computer systems and other devices can include server computer systems, desktop computer systems, laptop computer systems, netbooks, tablets, mobile phones, personal digital assistants, televisions, cameras, automobile computers, electronic media players, appliances, wearable devices, other hardware, and/or the like. In some embodiments, the facility may operate on specific-purpose computing systems, such as wide-band biopotential measuring equipment (or any device configured to capture unfiltered electrophysiological signals, including electrophysiological signals with unaltered spectral components), electroencephalogram equipment, radiology equipment, sound recording equipment, and so on. In various examples, the computer systems and devices include one or more of each of the following: a central processing unit ("CPU") configured to execute computer programs; a computer memory configured to store programs and data while they are being used, including a multithreaded program being tested, a debugger, the facility, an operating system including a kernel, and device drivers; a persistent storage device, such as a hard drive or flash drive configured to persistently store programs and data (e.g., firmware and the like); a computer-readable storage media drive, such as a floppy, flash, CD-ROM, or DVD drive, configured to read programs and data stored on a computer-readable storage medium, such as a floppy disk, flash memory device, CD-ROM, or DVD; and a network connection configured to connect the computer system to other computer systems to send and/or receive data, such as via the internet, a Local Area Network (LAN), a Wide Area Network (WAN), a point-to-point dial-up connection, a cell phone network, or another network and its networking hardware in various examples including routers, switches, and various types of transmitters, receivers, or computer-readable transmission media. While computer systems configured as described above may be used to support the operation of the facility, those skilled in the art will readily appreciate that the facility may be implemented using devices of various types and configurations, and having various components. Elements of the facility may be described in the general context of computer-executable instructions, such as program modules, executed by one or more computers or other devices. Generally, program modules include routines, programs, objects, components, data structures, and/or the like configured to perform particular tasks or implement particular abstract data types and may be encrypted. Furthermore, the functionality of the program modules may be combined or distributed as desired in various examples. Moreover, display pages may be implemented in any of various ways, such as in C++ or as web pages in XML (Extensible Markup Language), HTML (HyperText Markup Language), JavaScript, AJAX (Asynchronous JavaScript and XML) techniques, or any other scripts or methods of creating displayable data, such as the Wireless Access Protocol (WAP). Typically, the functionality of the program modules may be combined or distributed as desired in various embodiments, including cloud-based implementations, web applications, mobile applications for mobile devices, and so on.

The following discussion provides a brief, general description of a suitable computing environment in which the disclosed technology can be implemented. Although not required, aspects of the disclosed technology are described in the general context of computer-executable instructions, such as routines executed by a general-purpose data processing device, e.g., a server computer, wireless device, or personal computer. Those skilled in the relevant art will appreciate that aspects of the disclosed technology can be practiced with other communications, data processing, or computer system configurations, including: internet or otherwise network-capable appliances, hand-held devices (including personal digital assistants (PDAs)), wearable computers (e.g., fitness-oriented wearable computing devices), all manner of cellular or mobile phones (including Voice over IP (VoIP) phones), dumb terminals, media players, gaming devices, multi-processor systems, microprocessor-based or programmable consumer electronics, set-top boxes, network PCs, mini-computers, mainframe computers, and the like. Indeed, the terms "computer," "server," "host," "host system," and the like are generally used interchangeably herein, and refer to any of the above devices and systems, as well as any data processor.

Aspects of the disclosed technology can be embodied in a special purpose computer or data processor, such as application-specific integrated circuits (ASIC), field-programmable gate arrays (FPGA), graphics processing units (GPU), many core processors, and so on, that is specifically programmed, configured, or constructed to perform one or more of the computer-executable instructions explained in detail herein. While aspects of the disclosed technology, such as certain functions, are described as being performed exclusively on a single device, the disclosed technology can also be practiced in distributed computing environments where functions or modules are shared among disparate processing devices, which are linked through a communications network such as a Local Area Network (LAN), Wide Area Network (WAN), or the internet. In a distributed computing environment, program modules may be located in both local and remote memory storage devices.

Aspects of the disclosed technology may be stored or distributed on tangible computer-readable media, including magnetically or optically readable computer discs, hard-wired or preprogrammed chips (e.g., EEPROM semiconductor chips), nanotechnology memory, biological memory, or other computer-readable storage media. Alternatively, computer-implemented instructions, data structures, screen displays, and other data under aspects of the disclosed technology may be distributed over the internet or over other networks (including wireless networks), on a propagated signal on a propagation medium (e.g., electromagnetic wave(s), sound wave, etc.) over a period of time, or they may be provided on any analog or digital network (packet switched, circuit switched, or other scheme). Furthermore, the term computer-readable storage medium does not encompass signals (e.g., propagating signals) or transitory media.

Figure 3:
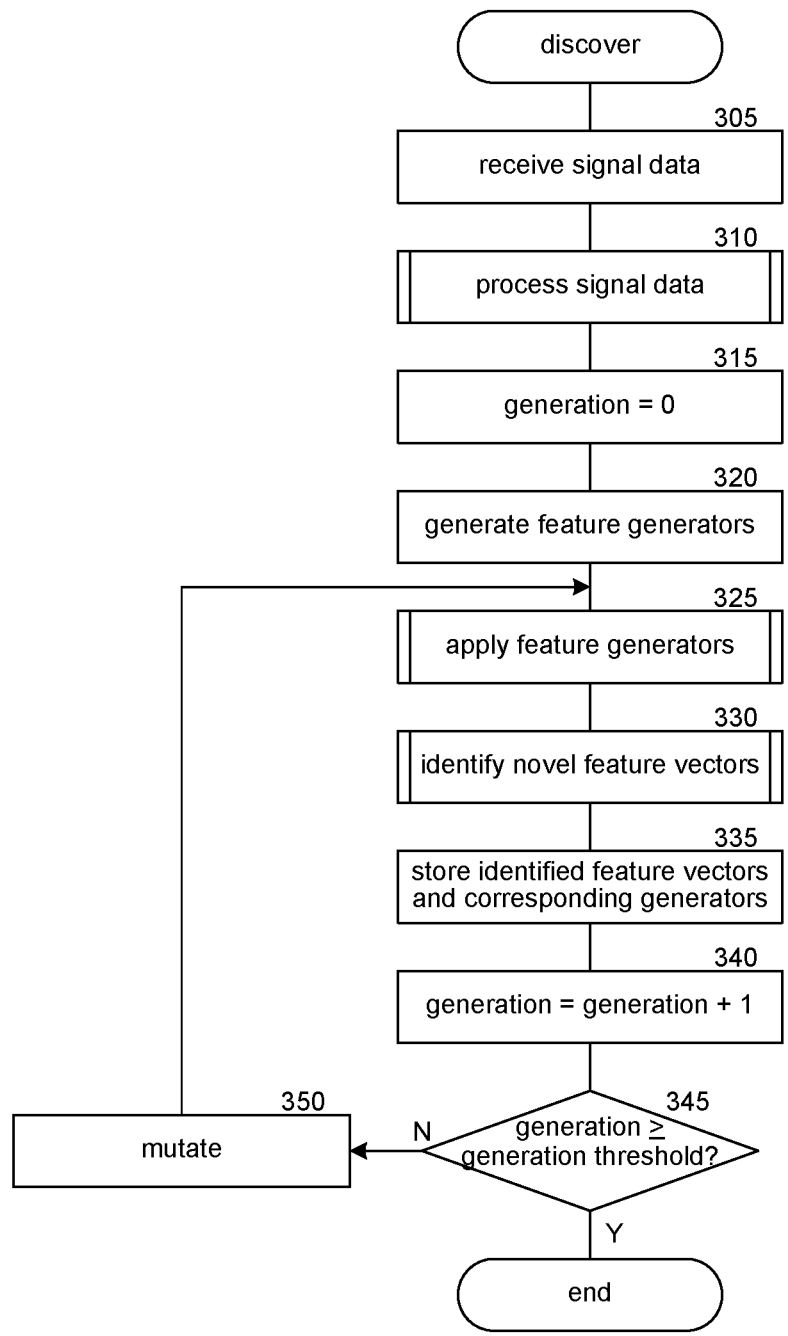
FIG. 3 is a flow diagram illustrating the processing of a discover component in some embodiments.

FIG. 3 is a flow diagram illustrating the processing of a discover component 221 in accordance with some embodiments of the disclosed technology. The discover component 221 is invoked by the facility to identify novel feature vectors based on selected patient data. In block 305, the component receives physiological signal data, such as raw signal data received directly from a signal recorder, previously-generated physiological signal from another device or site, etc. Several techniques exist for collecting and analyzing physiological signals (e.g., electrophysiological signals, biosignals) from patients for diagnostic and other purposes including, for example, activity trackers, echocardiograms, wide-band biopotential measuring equipment, electroencephalograms, electromyograms, electrooculography, galvanic skin response, heart rate monitors, magnetic resonance imaging, magnetoencephalograms, mechanomyograms, wearable technology devices (e.g., FITBITs), and so on. While data provided by these systems can be helpful in identifying medical concerns and diagnosing medical conditions, they are often only a starting point for the diagnosis process. Moreover, given the specific nature of most of these systems, the data they analyze is often over-filtered to reduce complexity for the system itself or for, e.g., a technician, physician, or other health care provider (in such cases, to reduce visual complexity, etc.) thereby eliminating data that potentially have untapped diagnostic value. In block 310, the component invokes a process signal data component to process and transform the received signal data, which can produce multiple sets of data and transformed data. In block 315, the component sets a generation value equal to 0. In block 320, the component generates one or more feature generators by, for example, randomly generating an expression tree, randomly generating a set of weights for a neural network, randomly mutating one or more of a set of previously-generated feature generators, and so on. In block 325, the component invokes an apply feature generators component to apply the generated feature generators to one or more sets of the processed signal data to produce a set of feature vectors. In block 330, the component invokes an identify novel feature vectors component to identify the most novel feature vectors from among the group of feature vectors generated by the feature generators. In block 335, the component stores the feature generators that produced the identified feature vectors in, for example, a feature generator store. In block 340, the component increments the generation variable. In decision block 345, if the generation variable is greater than or equal to a generation threshold, then the component completes, else the component continues at block 350. The component may also use other stopping conditions, such as a number of generations of feature generators that do not produce at least a threshold number of novel feature vectors. In block 350, the component copies and mutates the identified feature generators and then loops back to block 325 to apply the mutated feature generators to one or more sets of the processed signal data. As discussed above, the component may apply any type or types of mutations to a feature generator, such as applying multiple point mutations and/or a random recombination to one or more expression trees, randomly generating a set of connection weights for a neural network, and so on.

Figure 4:
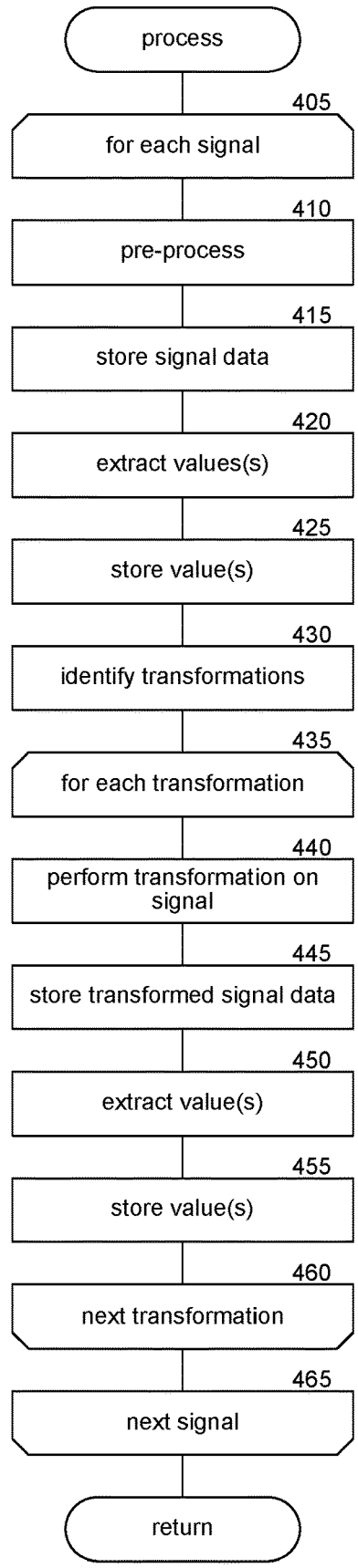
FIG. 4 is a flow diagram illustrating the processing of a process component in some embodiments.

FIG. 4 is a flow diagram illustrating the processing of a process component 222 in accordance with some embodiments of the disclosed technology. The process component 222 is invoked by the discover component to process and transform patient signal data. In blocks 405 through 465, the component loops through each signal (or data set) of a set of received signals (or set of data sets), each signal representing physiological data received from a patient. In block 410, the component pre-processes the received signal, such as applying one or more signal filters to the signal, performing a peak search on the data and discarding extraneous information, down-sampling the received signal, up-sampling the received signal, sub-sampling the received signal, converting an analog signal to a digital signal, converting image data to signal data, and so on. In block 415, the component stores the pre-processed signal in, for example, a patient data store. The signal data may be stored anonymously (i.e., without explicitly or implicitly identifying the corresponding patient, etc.). However, different instances of signal data associated with the same patient may be associated with an anonymized unique identifier so that multiple signals from a single patient can be used in conjunction for training and diagnostic purposes. In block 420, the component extracts one or more values from the stored signal data. In block 425, the component stores the one or more extracted values. In block 430, the component identifies any transformations to be applied to the signal. For example, the facility may store an indication of a set of transformations or transformation functions (e.g., Fourier transforms, functions to apply to the signal, derivatives, partial derivatives, and so on) to apply to a particular signal. As another example, the facility may randomly select, from among a catalog of transformations, one or more transformations to apply to the signal data. In blocks 435 through 460, the component loops through each of the transformations and applies the transformation to the signal data. In block 440, the component applies the transformation to the signal (e.g., calculating the third derivative with respect to a particular variable, calculating the result of a composite function generated by applying one function to the signal data (i.e., a function representative of the signal data), etc. In block 445, the component stores the transformed signal data in, for example, a patient data store. In block 450, the component extracts one or more values from the transformed signal data. In block 455, the component stores the one or more extracted values. In block 460, if there are any identified transformations yet to be applied, then the component selects the next transformation and loops back to block 435 to apply the transformation to the signal data, else the component continues at block 465. In block 465, if there are any signals yet to be analyzed, then the component selects the next signal and loops back to block 405 to process the next signal, else the component completes.

Figure 5:
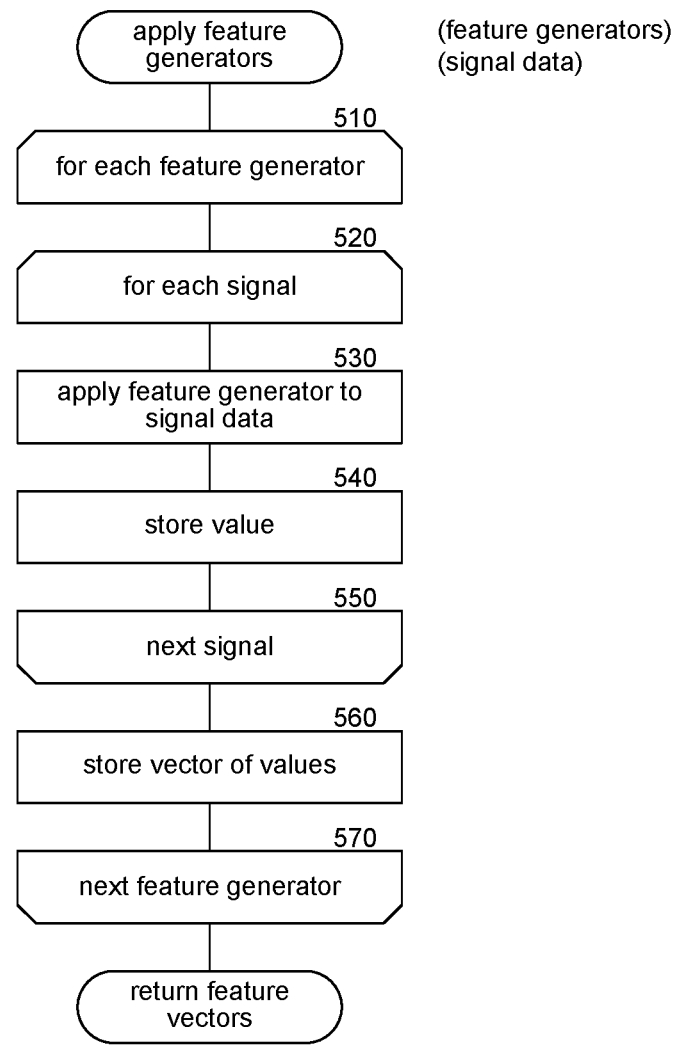
FIG. 5 is a flow diagram illustrating the processing of an apply feature generators component in some embodiments.

FIG. 5 is a flow diagram illustrating the processing of an apply feature generators component 223 in accordance with some embodiments of the disclosed technology. The apply feature generators 223 component is invoked by the discover component to apply a set of one or more feature generators to signal data, such as pre-processed and transformed signal data, modeled signal data, etc. In blocks 510 through 570, the component loops through each of a received set of feature generators and applies the feature generator to each signal in a received set of signal data. For example, the received signal data can include multiple sets of signal data for each of multiple patients, multiple transformations of that data, and so on. In blocks 520 through 550, the component loops through each of the signals to apply the feature generators to the signal data. In block 530, the component applies the currently-selected feature generator to the currently-selected signal data. For example, the component may apply the feature generator to each of a pre-processed version of the currently-selected signal data and any transformed version of that data. As another example, the component "plugs in" or substitutes coefficients generated by modeled signal data into a feature generator with a set of variables to produce an output feature value. As another example, the component can apply one or more elements of modeled signal data to a neural network to produce an output feature value. In block 540, the component stores the output value. In block 550, if there are any signals yet to be analyzed, then the component selects the next signal and loops back to block 520 to process the next signal, else the component continues at block 560. In block 560, the component generates a feature vector that includes each of the generated feature values and stores the feature vector in association with the feature generator in, for example, a feature vector store. For example, the feature vector may comprise an array of features and a link to, or identifier of, the corresponding feature generator. The component may also associate the feature vector with the signal data used to generate the feature vector. In block 570, if there are any feature generators yet to be processed, then the component selects the next feature generator and loops back to block 510 to process the feature generator, else the component returns the feature vectors.

Figure 6:
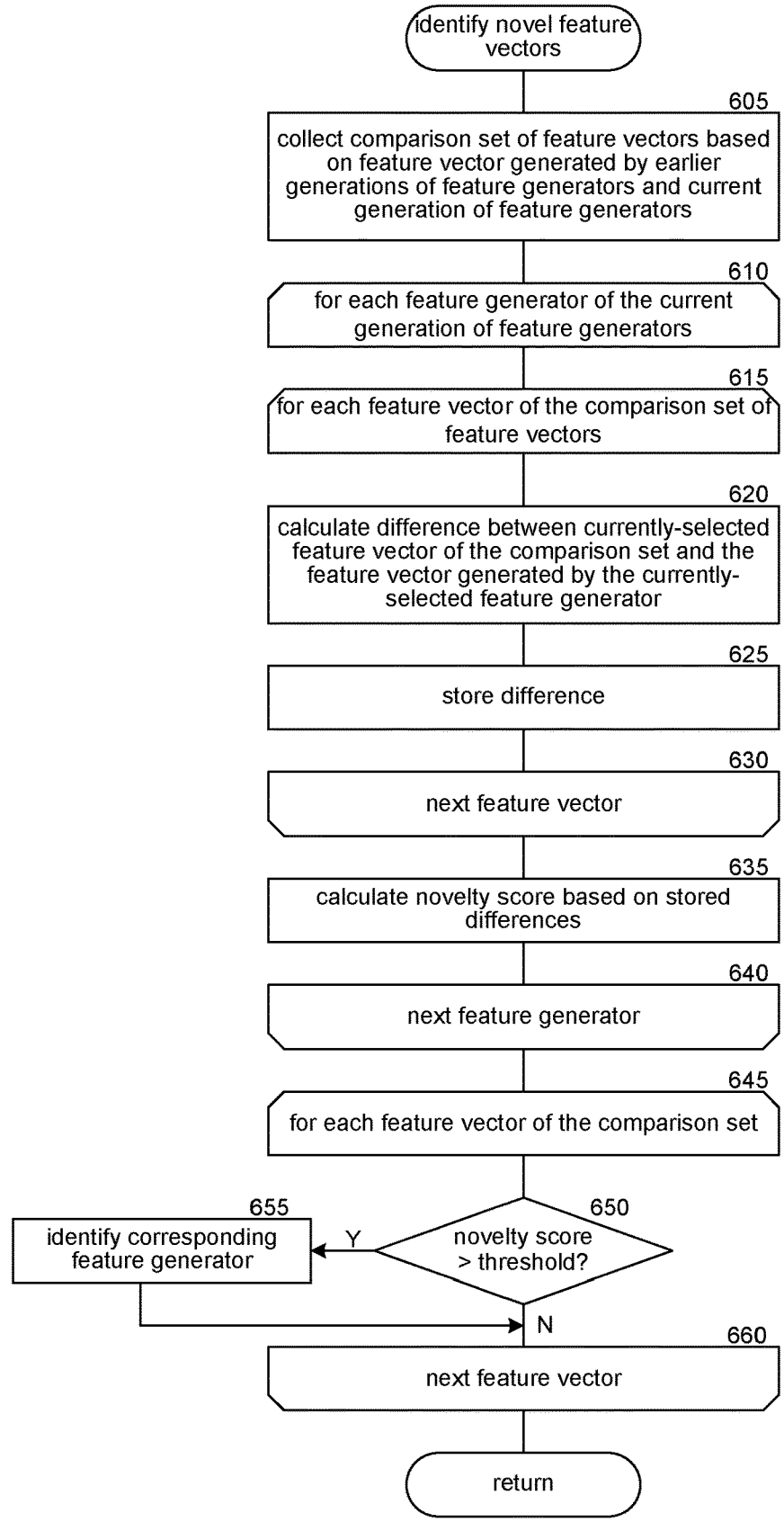
FIG. 6 is a flow diagram illustrating the processing of an identify novel feature vectors component in some embodiments.

FIG. 6 is a flow diagram illustrating the processing of an identify novel feature vectors component 224 in accordance with some embodiments of the disclosed technology. In this example, the facility receives a set of feature vectors and, for each feature vector, information related to the corresponding feature generator, such as an identifier for the feature generator. In block 605, the component collects a comparison set of feature vectors that includes, for example, feature vectors generated by feature generators of earlier generations that were found to be novel and the feature vectors generated by a current generation of feature vectors. For example, the component can randomly select a set of novel feature vectors from a feature store. In some cases, a request to retrieve feature vectors includes upper and lower limits on the number of features values for each feature vector to be retrieved, such as no less than 50 (lower threshold) and no more than 5000 (upper threshold). In blocks 610 through 640, the component loops through each feature vector of a current generation of feature generators to determine how different each of their corresponding feature vectors is to each of the feature vectors of the comparison set of feature vectors. In blocks 615 through 630, the component loops through each feature vector of the comparison set of feature vectors to compare each feature vector to the feature vector of the currently-selected feature generator. In block 620, the component calculates a difference value between the currently-selected feature vector of the comparison set and the feature vector of the currently-selected feature generator. For example, the component can calculate a distance value between each of the feature vectors. In block 625, the component stores the calculated difference value. In block 630, if there are any feature vectors yet to be compared, then the component selects the next feature vector and loops back to block 615 to process the feature vectors, else the component continues at block 635. In block 635, the component calculates a novelty score for the currently-selected feature generator based on the stored difference values; such as an average or maximum distance and stores the novelty score in association with the feature generator (e.g., in a feature generator store). In block 640, if there are any feature generators yet to be assessed, then the component selects the next feature generator and loops back to block 615 to process the feature generator, else the component continues at block 645. In blocks 645 through 660, the component tests whether each of the feature vectors is novel, based on the calculated novelty scores, and identifies any corresponding feature generators. In decision block 650, if the novelty score for the currently-selected feature generator is greater than a novelty threshold, then the component continues at block 655, else the component continues at block 660. The novelty threshold may be generated or determined in any number of ways, such as receiving a novelty threshold from a user, calculating a novelty threshold based on the set of novelty scores (e.g., average, average plus 25%, top n (where n is provided by a user or generated automatically by the facility), top tenth percentile), and so on. In this manner, the novelty threshold may change dynamically (e.g., from generation to generation) based on, for example, the number of generations without a new feature generator that exceeds the current novelty threshold to ensure that the facility is producing and testing new feature generators and corresponding features. In block 655, the component identifies the currently-selected feature vector as novel. In block 660, if there are any feature vectors yet to be processed, then the component selects the next feature vector and loops back to block 645 to process the feature vector, else the component completes.

From the foregoing, it will be appreciated that specific embodiments of the disclosed technology have been described herein for purposes of illustration, but that various modifications may be made without deviating from the scope of the disclosed technology. For example, the disclosed techniques can be applied to fields outside of the medical field, such as predicting weather patterns, geological activity, or any other field in which predictions are made based on sampled input data. To reduce the number of claims, certain aspects of the disclosed technology are presented below in certain claim forms, but applicants contemplate the various aspects of the disclosed technology in any number of claim forms. Accordingly, the disclosed technology is not limited except as by the appended claims.

We claim:

1. A system for discovering features for use in machine learning to diagnose one or more medical conditions within one or more patients, the system comprising:
   a machine configured to receive physiological signal data from at least one patient;
   a first component configured to store the received physiological data in a patient data store, the patient data store comprising physiological data for a plurality of patients;
   a second component configured to, for each of one or more of the plurality of patients,
      receive, from the patient data store, one or more types of physiological signal data for the at least one patient, each type of physiological signal data representing at least one physiological output of the corresponding patient, and
      for each type of the received physiological signal data, extract at least one value from the corresponding physiological data signal;
   a third component configured to, for each type of physiological data,
      for each of the one or more patients for which the type of physiological data was received,
         apply a plurality of feature generators to the at least one value extracted from the corresponding physiological data to generate a feature for the type of physiological data, and
      generate, based on the generated features, a plurality of feature vectors for the type of data;
   a fourth component configured to, for each generated feature vector,
      calculate a novelty score for the feature vector;
   a fifth component configured to identify, from among the plurality of feature vectors, at least one novel feature vector based on the calculated novelty scores, wherein novelty is determined by comparing a novelty score to a novelty threshold;
   a sixth component configured to identify each feature generator from among the plurality of feature generators that generated a novel feature vector; and
   a seventh component configured to mutate each of the identified feature generators to produce another feature generator generation.

2. The system of claim 1, wherein the machine comprises wide-band biopotential measuring equipment.

3. A computer-readable medium storing instructions that, if executed by a computing system having a memory and a processor, cause the computing system to perform a method for discovering features for use in machine learning, the method comprising:
   for each of a plurality of feature generators,
      for each of a plurality of data signals,
         extracting values from the data signal, and
         applying the feature generator to the extracted values to produce a feature value, and
      generating, by the feature generator, a feature vector based on the produced feature values;
   for each feature vector of a plurality of generated feature vectors,
      calculating a novelty score for the feature vector;
      identifying, from among the plurality of feature vectors, at least one novel feature vector based on the calculated novelty scores, wherein identifying the at least one novel feature vector comprises comparing a novelty score to a novelty threshold; identifying each feature generator from among the plurality of feature generators that generated a novel feature vector; and mutating each of the identified feature generators to produce another feature generator generation.

4. The computer-readable medium of claim 3, the method further comprising:
   randomly generating the plurality of feature generators, wherein generating a first feature generator comprising an expression tree comprises:
      generating a binary tree comprising a plurality of nodes, and
      for each of the plurality of nodes,
         assigning an operator, value, or equation to the node.

5. The computer-readable medium of claim 3, the method further comprising:

randomly generating the plurality of feature generators, wherein generating a first feature generator comprising a neural network comprises:
for each of a plurality of connections weights of the neural network, randomly generating a value.

6. The computer-readable medium of claim 3, wherein mutating a first feature generator comprises applying at least one of a point mutation, random recombination, sub-tree mutation, or any combination thereof to the first feature generator.

7. The computer-readable medium of claim 3, wherein calculating a novelty score for a first feature vector comprises:
for each of a plurality of feature vectors other than the first feature vector, calculating a difference value between the first feature vector and the feature vector other than the first feature vector; and
aggregating the calculated difference values.

8. The computer-readable medium of claim 7, wherein aggregating the calculated difference values comprises computing an average value based on the calculated difference values.

9. The computer-readable medium of claim 3, the method further comprising:
applying a mutated feature generator to at least one representation of physiological data provided by at least one patient.

10. The computer-readable medium of claim 3, wherein mutating a first feature generator comprises applying a sub-tree mutation to the first feature generator.

11. A method, performed by a computing system having a memory and a processor, for discovering features for use in machine learning, the method comprising:
for each of a plurality of feature generators,
for each of a plurality of data signals,
extracting values from the data signal, and
applying the feature generator to the extracted values to produce a feature value, and
generating, by the feature generator, a feature vector based on the produced feature values;
for each of a plurality of generated feature vectors,
calculating a novelty score for the feature vector; identifying, from among the plurality of feature vectors, at least one novel feature vector based on the calculated novelty scores, wherein identifying the at least one novel feature vector comprises comparing a novelty score to a novelty threshold; identifying each feature generator from among the plurality of feature generators that generated a novel feature vector; and mutating each of the identified feature generators to produce another feature generator generation.

12. The method of claim 11, further comprising:
computing the novelty threshold at least in part by, determining an average novelty score based on the calculated novelty scores.

13. The method of claim 11, further comprising:
computing the novelty threshold at least in part by, determining a n-th percentile of novelty scores based on the calculated novelty scores.

14. The method of claim 11, further comprising:
computing the novelty threshold at least in part by, determining an n-th highest novelty score from among the calculated novelty scores.

15. The method of claim 11, further comprising:
generating a predictive model based at least in part on the identified at least one novel feature vector.

16. The method of claim 15, further comprising:
for each of a plurality of input signals, each signal corresponding to a patient,
predicting an outcome for the corresponding patient based at least in part on the generated predictive model.

* * * * *

UNITED STATES PATENT AND TRADEMARK OFFICE
CERTIFICATE OF CORRECTION

Page 1 of 1

PATENT NO. : 11,139,048 B2
APPLICATION NO. : 15/653433
DATED : October 5, 2021
INVENTOR(S) : Grouchy et al.

It is certified that error appears in the above-identified patent and that said Letters Patent is hereby corrected as shown below:

On the Title Page

Item (72), in Column 1, in "Inventors", Line 2, delete "Ottowa" and insert -- Ottawa --, therefor.

Item (56), page 3, Column 1, under "Other Publications", Line 10, delete "Amaldo," and insert -- Arnaldo, --, therefor.

In the Specification

In Column 1, Line 10, delete "14/970,580," and insert -- 13/970,580, --, therefor.

In Column 9, Line 48, delete "3-D" and insert -- 3D --, therefor.

In the Claims

In Column 16, Line 15, in Claim 1, after "of" insert -- physiological --.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*